(12) United States Patent
Boveja et al.

(10) Patent No.: US 7,578,816 B2
(45) Date of Patent: Aug. 25, 2009

(54) METHOD AND SYSTEM OF INCREASING SAFETY OF CARDIAC ABLATION PROCEDURES

(75) Inventors: Birinder R. Boveja, Milwaukee, WI (US); Angely Widhany, Milwaukee, WI (US)

(73) Assignee: ABL Technologies, LLC, Milwaukee, WI (US)

( * ) Notice: Subject to any disclaimer, the term of this patent is extended or adjusted under 35 U.S.C. 154(b) by 611 days.

(21) Appl. No.: 11/112,648

(22) Filed: Apr. 22, 2005

(65) Prior Publication Data

US 2005/0177053 A1    Aug. 11, 2005

(51) Int. Cl.
*A61B 18/04* (2006.01)

(52) U.S. Cl. .................. 606/34; 600/508; 600/509; 606/42; 607/119; 607/122

(58) Field of Classification Search ......... 600/508–528; 606/34, 39, 41, 42; 607/122, 119
See application file for complete search history.

(56) References Cited

U.S. PATENT DOCUMENTS

| | | | |
|---|---|---|---|
| 5,507,743 A | 4/1996 | Edwards et al. | 606/41 |
| 5,837,001 A * | 11/1998 | Mackey | 607/102 |
| 6,679,269 B2 | 1/2004 | Swanson | 128/898 |
| 6,730,078 B2 * | 5/2004 | Simpson et al. | 606/34 |
| 2004/0059237 A1 * | 3/2004 | Narayan et al. | 600/509 |
| 2004/0127894 A1 | 7/2004 | Eick et al. | 606/34 |
| 2005/0148892 A1 * | 7/2005 | Desai | 600/510 |

OTHER PUBLICATIONS

Kottkamp et al. "An anatomically and electrogram-guided stepwise approach for effective and safe catheter ablation of the fast pathway for elimination of atrioventricular node reentrant tachycardia." Apr. 1995, Journal of the American College of Cardiology; 25:974-81.*

* cited by examiner

*Primary Examiner*—Michael Peffley
*Assistant Examiner*—Vincent Sica

(57) ABSTRACT

Method and system of increasing safety of ablation of cardiac arrythmias, especially AVNRT and antero-septal accessory pathway ablations. A computer based system acquires, conditions, and analyzes the timing relationships between atrial and ventricualr signals during normal sinus (NSR) and junctional rhythms (JR) during ablation. If the timing analyses determines a safety issue, such as loss of retrograde conduction during junction rhythm, while slow pathway modification is being performed, the computer electronically disconnects the ablation circuit. This immediately stops the energy delivery to the tissues and provides a chance to reposition the ablation catheter tip to a more safer location. The ablation may be using radiofrequency (RF), cryoablation, or with high intensity focused ultrasound (HIFU). The functionality and circuitry of the system may also be incorporated within an ablation generator, EP recording and monitoring system, or a cardiac mapping system.

17 Claims, 22 Drawing Sheets

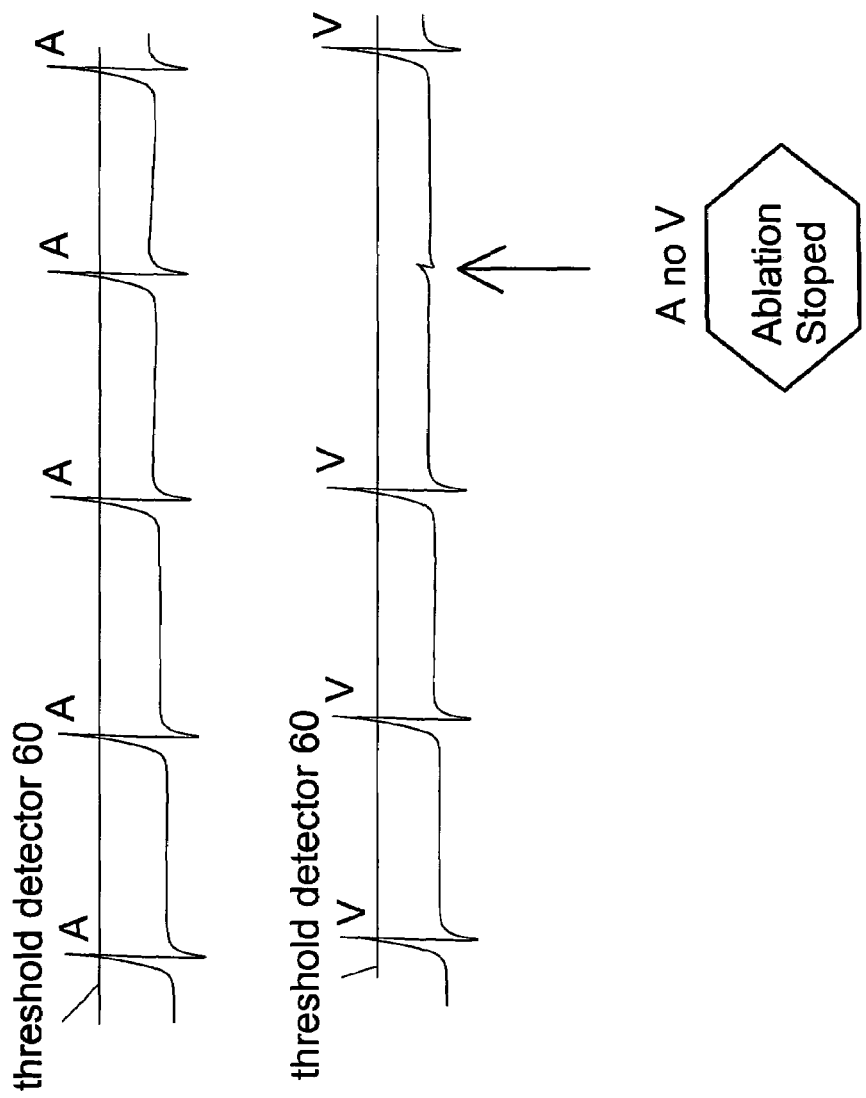

METHOD AND SYSTEM OF INCREASING SAFETY OF CARDIAC ABLATION PROCEDURES

FIELD OF INVENTION

The present invention relates to cardiac ablation, more specifically method and system for increasing the safety of transcatheter ablations for certain cardiac arrhythmia's.

BACKGROUND

Many cardiac arrhythmia's that formerly required the use of potentially toxic drugs or cardiac surgery can now be routinely cured (or at least palliated) in the electrophysiology laboratory by means of transcatheter ablation techniques. As shown in conjunction with FIG. 1, the basic idea behind transcatheter ablation is to position an electrode catheter to a critical area within the heart 52, and to apply damaging energy through the catheter in order to create a discrete scar. Strategically placed scar tissue, since it is electrically inert, can disrupt the pathways necessary for pathologic tachyarrhythmias.

A novel PC based system disclosed here, interfaces with both the patient and the ablation generator for providing added safety to the ablation procedure. Such a system finds uses in different types of cardiac ablation procedures, particularly left atrial ablations for atrial fibrillation, and slow pathway modification for providing ablation therapy of AV nodel reentry tachycardia.

A V nodal reentrant tachycardia (AVNRT) is the most common type of reentrant supraventricular tachycardia, and is the operative mechanism in up to 60% of patients presenting with paroxysmal atrial tachycardia (PAT). In AV nodal reentry, the reentrant circuit is usually said to be enclosed within the AV node. In patients with AV nodal reentry, the AV node is functionally divided into two longitudinal pathways (dual AV nodal pathways). These dual pathways form the reentrant circuit. Because the reentrant circuit in AV nodal reentry, for all practical purposes, involves the AV node exclusively, this arrhythmia responds well to autonomic maneuvers and drugs that affect the AV node (digitalis, calcium blockers, and β blockers). Ablation for AV nodal reentry tachycardia is typically performed using radiofrequency (RF) catheter ablation, or cryoablation.

During the past decade, RF ablation and cryoablation has become the treatment of choice for AV nodal reentrant tachycardia. Successfully ablating AV nodal reentrant tachycardia has required a change in the way electrophysiologists visualize the AV node. In the past, most electrophysiologists thought of the AV node simply as a compact, button-like structure. The AV node does indeed appear to have a compact distal component (i.e, the part of the node that gives rise to the His bundle), but the more proximal portion of the AV node appears to be "diffuse".

The tracts of atrial fibers that coalesce to form the AV node are ill defined. It now appears that (at least in patients with AV nodal reentrant tachycardia and probably in all individuals), two distinct tracts can be localized anatomically—the anterior tract (which corresponds to the fast AV nodal pathway), and the posterior tract (which corresponds to the slow AV nodal pathway).

In patients with AV nodal reentrant tachycardis, the fast and slow pathways can be visualized as two tracts of atrial fibers that coalesce to form the compact AV node. The fast pathway is an anterior and superior tract of fibers, located along the tendon of Todaro. The slow pathway is a posterior and inferior tract of fibers, located along the tricuspid annulus near the os of the coronary sinus. Thus, the anatomic correlate of the "functional" dual AV nodal pathways have now been identified. Because the two pathways can be discretely localized, they can be discretely ablated. Even though the fast pathway can also be ablated, the ablation of AV nodal reentry is now generally accomplished by ablating the slow pathway, since the slow pathway is posterior, and relatively distinct from the AV node.

Even though the success rate of AVNRT ablation is very high, many patients end up with heart block. The heart block may be temporary or permanent. Patients with temporary heart block recover, however if patients AV conduction does not recover spontaneously, a cardiac pacemaker and lead(s) are implanted. These patients become pacemaker dependent for the rest of their lives. Considering that some of these patients are relatively young, there is a real need for a method and system that would increase the safety of cardiac ablation procedures, especially for common ablation procedures, such as ablations for AVNRT and atrial fibrillation.

This patent application is directed to novel method and system for monitoring the ablation procedure, and under certain conditions either shutting off power to the ablation generator or disconnecting the ablation circuit, whereby preventing excessive energy to get to the cardiac tissues, and reducing and/or eliminating the chances of developing complete heart block in AV nodal reentry tachycardia ablation procedures.

PRIOR ART

Prior art search reveals U.S. Pat. No. 0,127,894 A1 (Eick et al.), which is generally directed to ablation catheter operation feedback, thereby providing the clinicians with increased options for programmable control of the ablation catheter.

The Eick '894 patent application mainly discloses using LocaLisa mapping system for monitoring the location and movement of the ablation catheter. The applicant's invention is directed to monitoring the patient's electrograms and the relationship between electrograms using an ablation interface system, which is a totally different concept.

Another important distinction is that the Eick '894 patent application is limited to use with RF ablation system only. The applicant's method and system may be used with RF or any other type of ablation system such as cryoablation. This is relevant because a significant percentage of physicians are starting to use Cryoablation system for AVNRT ablation therapy.

SUMMARY OF THE INVENTION

The current invention discloses a novel method and system of increasing safety of cardiac ablation procedures such as ablation for AV nodal reentry tachycardis and antero-septal pathway ablation. One objective of the invention is to reduce or eliminate the chances of a patient getting heart blocked inadvertently during the procedure.

Accordingly, in one aspect of the invention the system acquires, conditions, and analyzes timing information of atrial and ventricular intracardiac signals. Based on pre-determined timing analyses, the system being capable of electronically switching off the ablation energy.

In another aspect of the invention, the system stops the ablation procedure by disconnecting the ablation circuit via the ground patch connection.

In another aspect of the invention, the system shuts off ablation by turning off power of the ablation generator.

In another aspect of the invention, the system performs timing analysis of atrial and ventricular intracardiac signals software program can be written utilizing development tools and graphical programming applications or languages such as, LAB WINDOWS/CVI®, LAB VIEW® (National Instruments Corp.), MICROSOFT VISUAL C++®, DOT NET FRAMEWORK®, MATLAB®, MICROSOFT VISUAL BASIC®.

In another aspect of the invention, the system may be incorporated into an ablation generator.

In another aspect of the invention, the system may be incorporated into an electrophysiology recording system.

In yet another aspect of the invention, the software program for analyzing intracardiac timing relationships can be modified.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 11C depicts intracardiac electrograms showing V and no A during junctional rhythm while ablation is on.

FIG. 11D depicts intracardiac electrograms showing A and no V during slow junctional rhythm while ablation is on.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
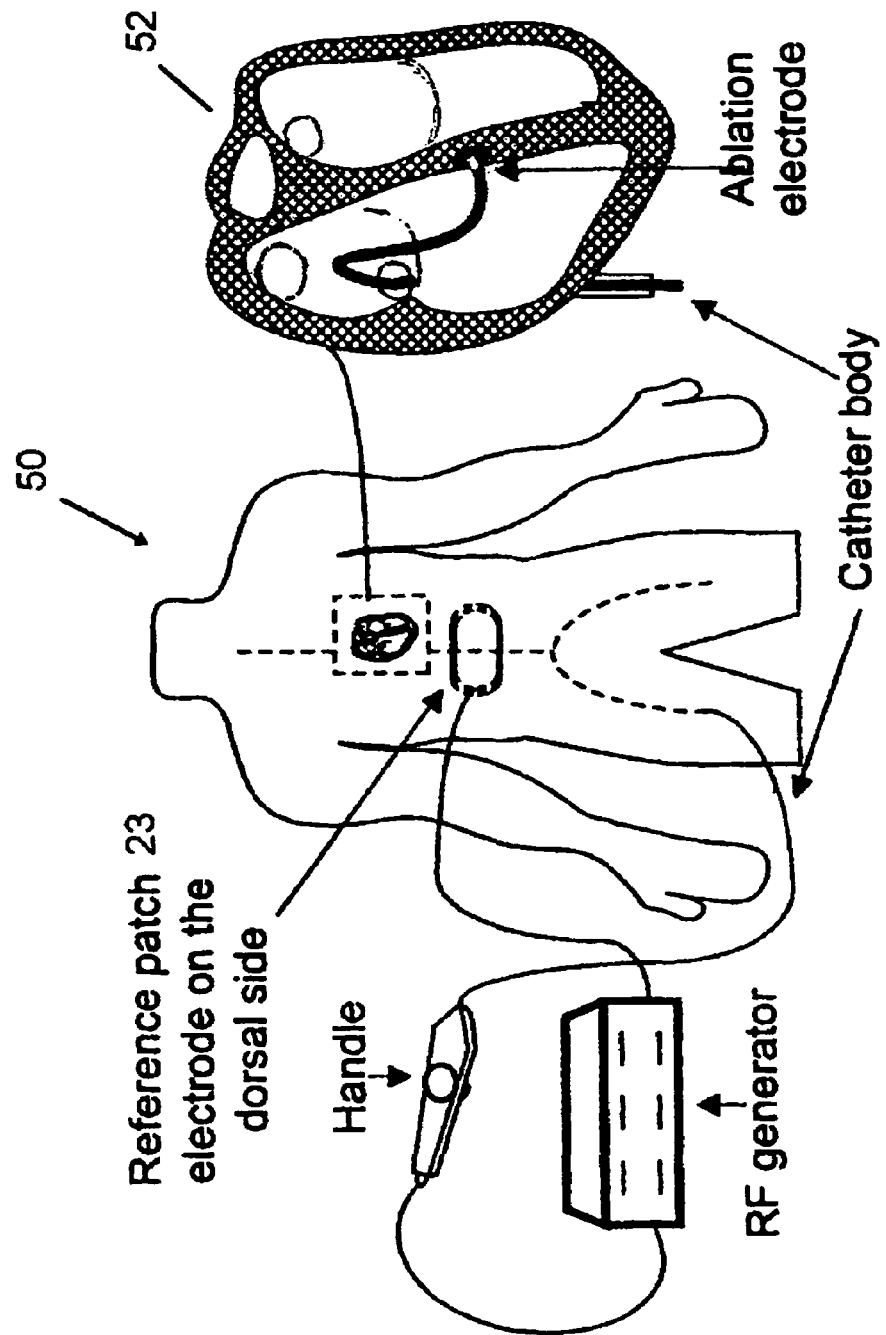
FIG. 1 depicts general concept for cardiac ablation procedures.
Figure 2:
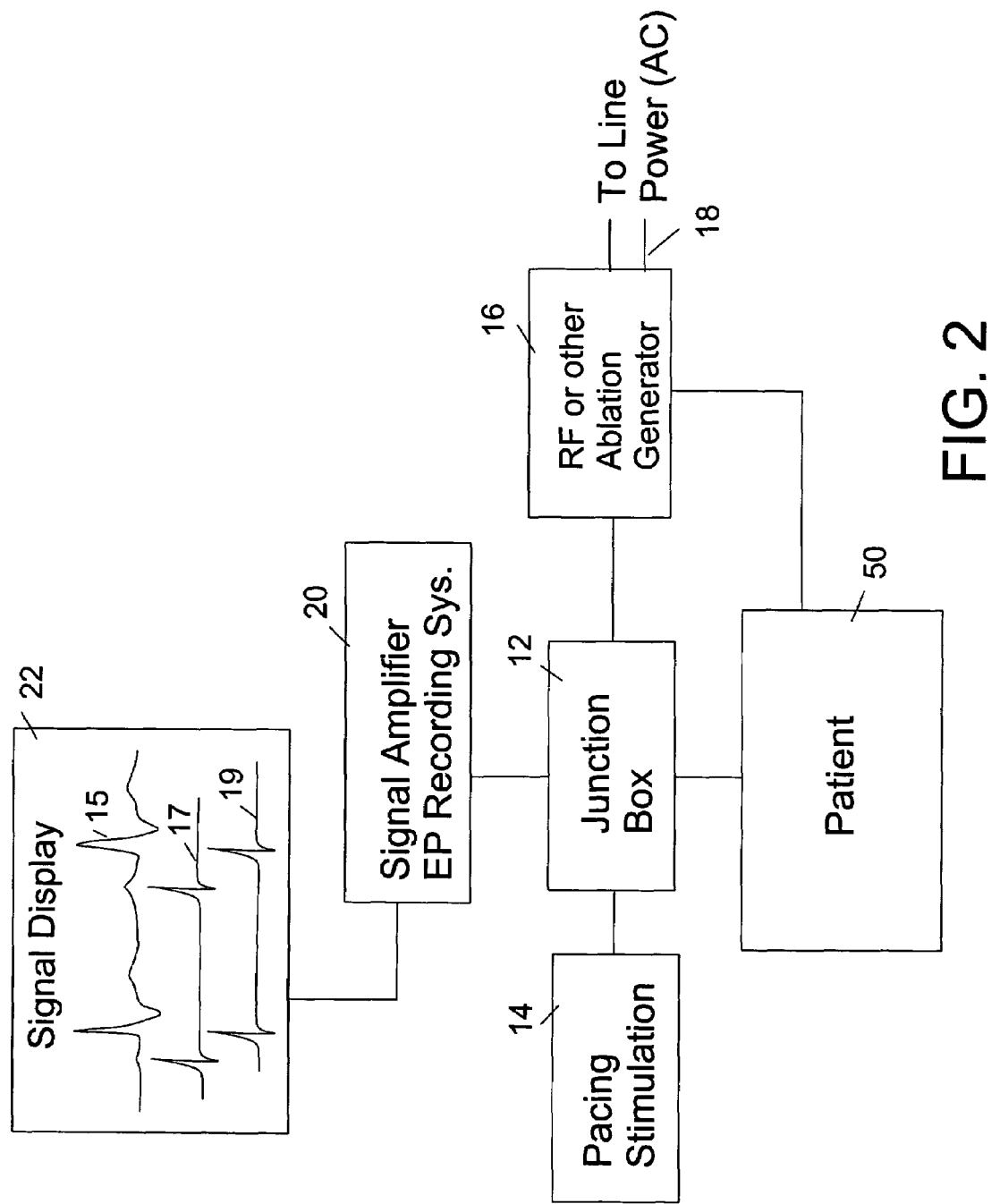
FIG. 2 depicts a general setup of cardiac ablation procedures.

For the purposes of explaining the methodology of the current invention, it is instructive to understand a typical setup for a generic cardiac ablation procedure. Shown in conjunction with FIG. 2 is a typical setup, where body surface ECG 15 (usually 12 lead), atrial intra-cardiac (IC) signal 17, ventricular intra-cardiac (IC) signal 19, and other intra-cardiac (IC) signals such as His bundle recording (not shown) and coronary sinus signals (not shown) are obtained from the patient 50, via transvenous diagnostic catheters. The catheters in the body are connected via extension cables to a junction box 12. The body surface signals are typically amplified by amplifiers of an EP recording system 20 and displayed on a display monitor 22 for easy visualization during the Electrophysiology (EP) study and cardiac ablation procedure. A pacing stimulator 14 is also connected (typically via junction box 12) for pacing of different sites within the heart such as the atrium or ventricle for example. An ablation generator 16 is connected to the patient 50. If a radiofrequency (RF) generator is used, a ground patch 23 or reference patch 23 which is typically connected on patient's back (FIG. 1) is connected to the RF ablation generator, and an ablation catheter 37 positioned inside the heart 52 and connected to the RF ablation generator 16 via connector cables completes the circuit for ablation procedure to proceed.

Typically a physician manipulates and positions the ablation catheter while being next to the patient's table, and another person operates the ablation generator 16. The ablation generator may be radiofrequency (RF), cryoablation, microwave, high intensity focused ultrasound (HIFU), or other forms of ablation. The physician positioning the ablation catheter is also able to operate the ablation generator via a foot paddle, even though that is typically not done.

In certain ablation procedures such as for A-V nodel re-entry tachycardia (AVNRT) or antero-septal accessory pathway ablation, it is imperative to stop the ablation generator energy after the first A-V disassociated beat. In the current clinical practice it can frequently take 2 to 5 seconds (sometimes even more) to stop the ablator energy, since the physician has to recognize the dropped (A-V) beat, communicate it to the person operating the ablation generator, and the reaction time of the person operating the ablation generator 16. The 2 to 5 seconds that it frequently takes, puts the patient at risk for complete heart block (A-V block), which may necessitate implantation of a cardiac pacemaker for maintaining patient's cardiac rhythm.

It is highly desirable to have a method and system where after sensing one atrial-ventricular blocked, the power of the ablation generator is interrupted immediately without the delay of the human reaction time. It is known from clinical experience, that where ablation power is interrupted after the first (A-V) dropped beat, the likelihood for the patient developing complete heart block is not very significant, thereby avoiding cardiac pacemaker implantation.

In the method and system of this invention, a computer based interface device performs analysis of the relationship between atrial and ventricular signals, and after sensing one disassociated beat between atrial and ventricular signals, the device automatically activates a switch which disconnects or removes power from the ablation generator whereby disrupting ablation generator energy. This allows for the physician to reposition ablation catheter to a slightly different position within the heart, reset the device and ablation generator 16, and start delivering ablation energy again. This procedure can be repeated as many times as necessary until the desired end point of the ablation is reached.

Figure 3:
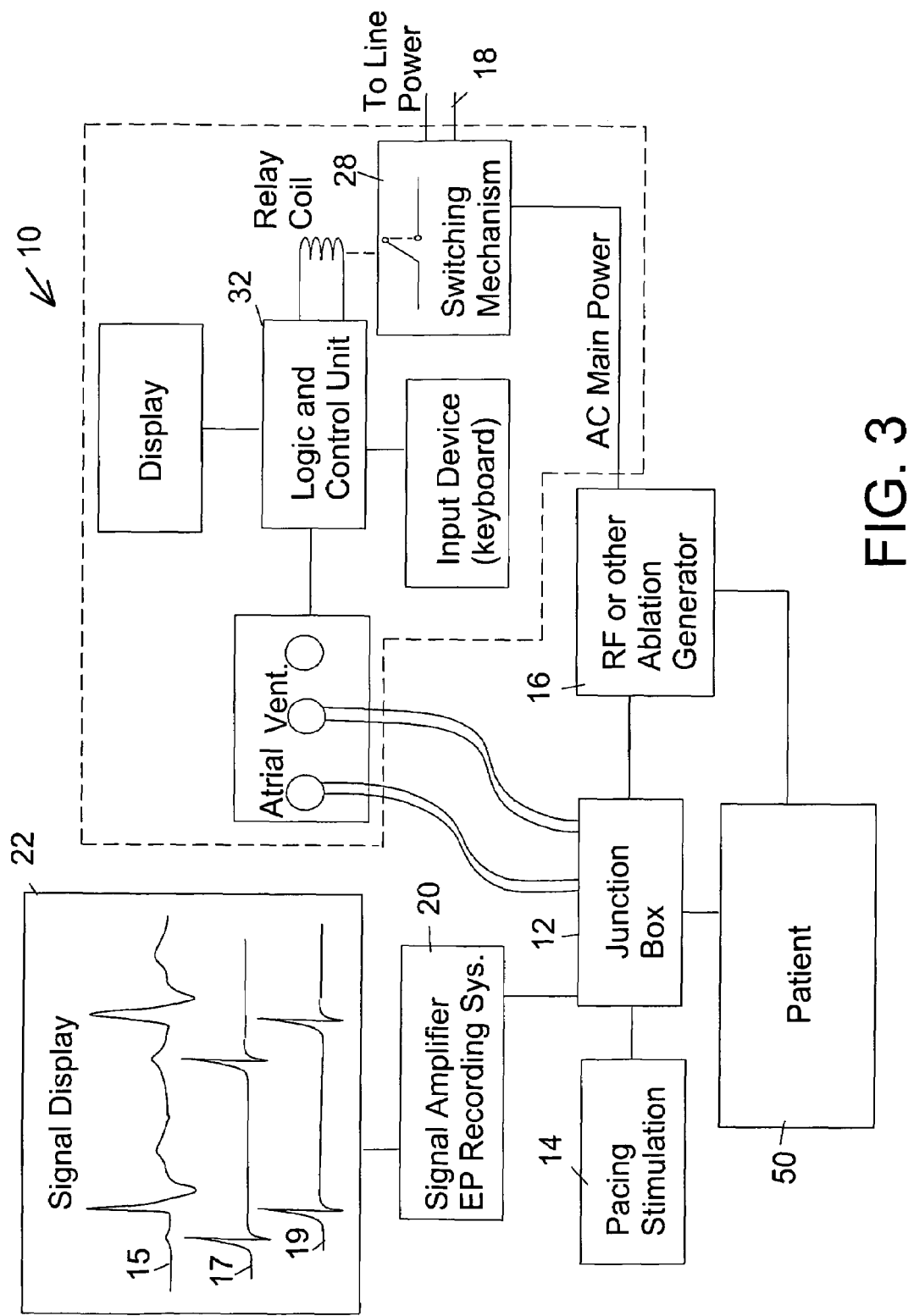
FIG. 3 depicts a general cardiac ablation setup with the concept ablation interface device (AID) 10.

Shown in conjunction with FIG. 3 is a simplified block diagram for the method and system (AID 10) of the current invention, and its relationship to other equipment during an EP ablation procedure. In the ablation interface device (AID) 10, the atrial and ventricular signals are jumped ("slaved") from the junction box 12 to the Ablation Interface Device 10 (AIP), via connecting cables. This is common practice in electrophysiology (EP) ablation procedures as intracardiac (IC) and Body Surface (BS) ECG signals are frequently exchanged between cardiac mapping systems and EP recording system. The atrial signals are typically in the 0.5-3 mV range, depending mostly upon contact with atrial tissue wall, and the viability of the atrial tissue of the heart muscle itself. Ventricular signals (usually from the RV apex) are typically in the 1-15 mV range, again depending mostly one tissue contact, and tissue viability. Atrial signals and ventricular signals, if small, may be amplified by the AID 10. The relationship (or lack of relationship) between the Atrial (A) and Ventricular (V) signals is analyzed by the controller 32 of the AID 10 and used to stop power to the ablation generator 16 circuit if there is a dropped beat, or a disassociation between the atrial and ventricular activity.

As shown in the block diagram, on one embodiment, the power of the ablation generator 16 is connected to the power line 18 via a switching mechanism 28. At an overall level, the switch is in the ON position before the ablation generator is energized to deliver energy via an ablation catheter 37. An AND gate, receiving input from ablation generator and signal from controller keeps the switch 28 in the closed position which keeps power to the ablation generator as long as both A and V signals are coupled to each other. At the first dropped beat, meaning when an A signal is not associated with a V signal or a V signal is not associated with an A signal, the logic and control unit 32 sends a command signal which trips the switch 28 into open position, whereby disconnecting energy to the ablation catheter. The tip of the ablation catheter ceases to ablate the heart tissue. When the catheter is repositioned to a safer position within the heart, the switch 28 is reset, and ablation can be attempted again.

Figure 4:
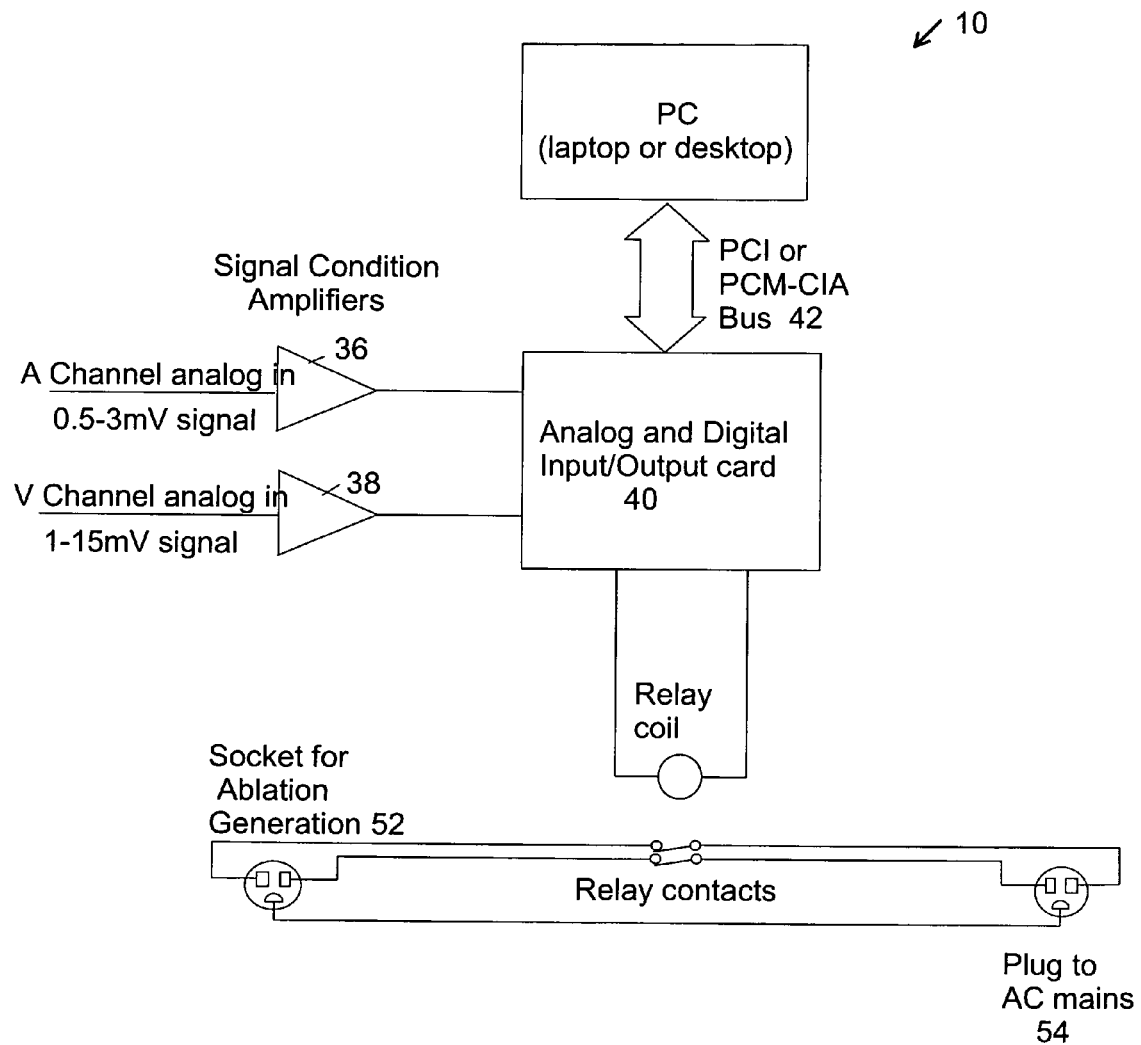
FIG. 4 is a simplified block diagram of one embodiment the invention (AID 10).
Figure 5A:
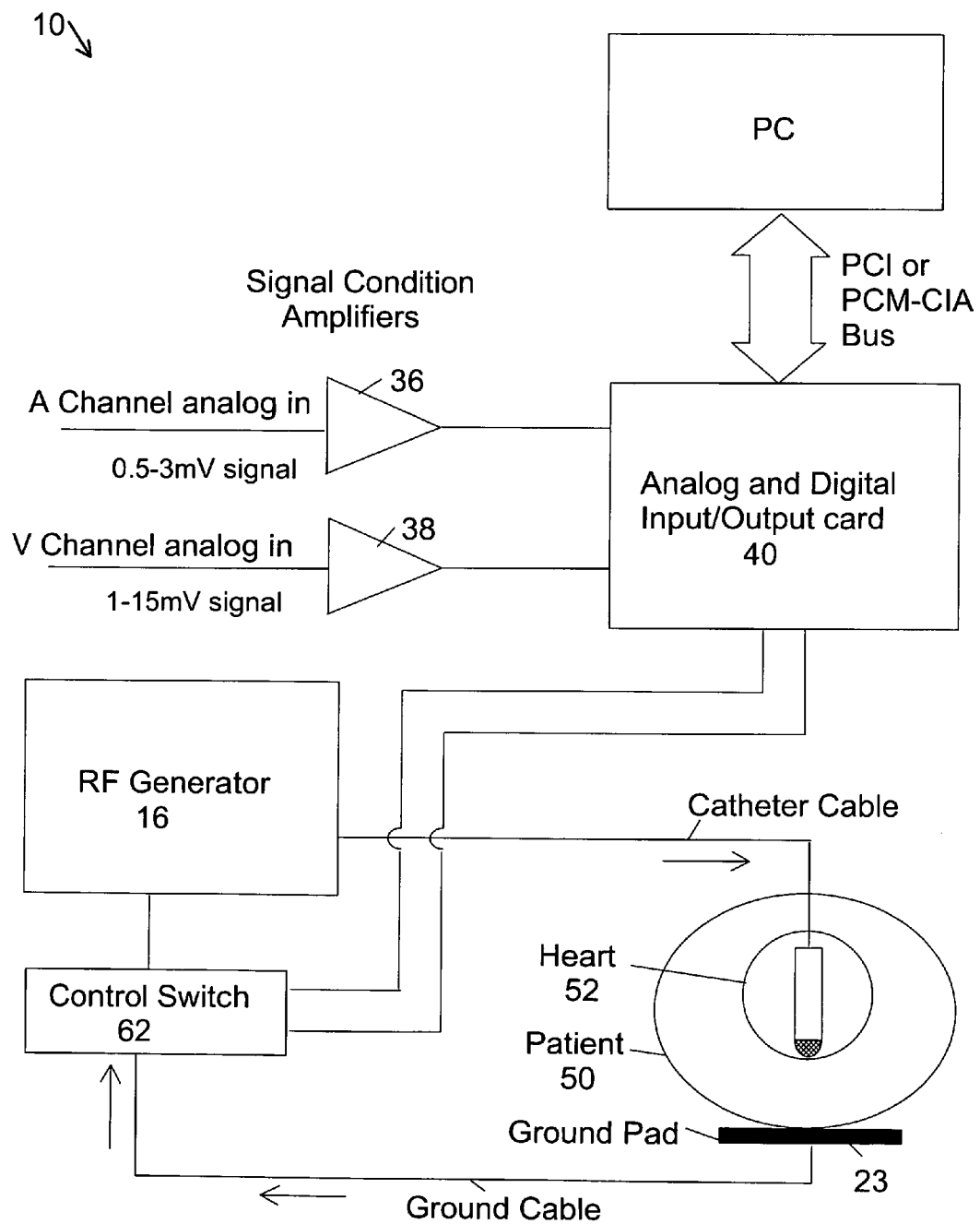
FIGS. 5A and 5B are two other embodiments of the invention.
Figure 5B:
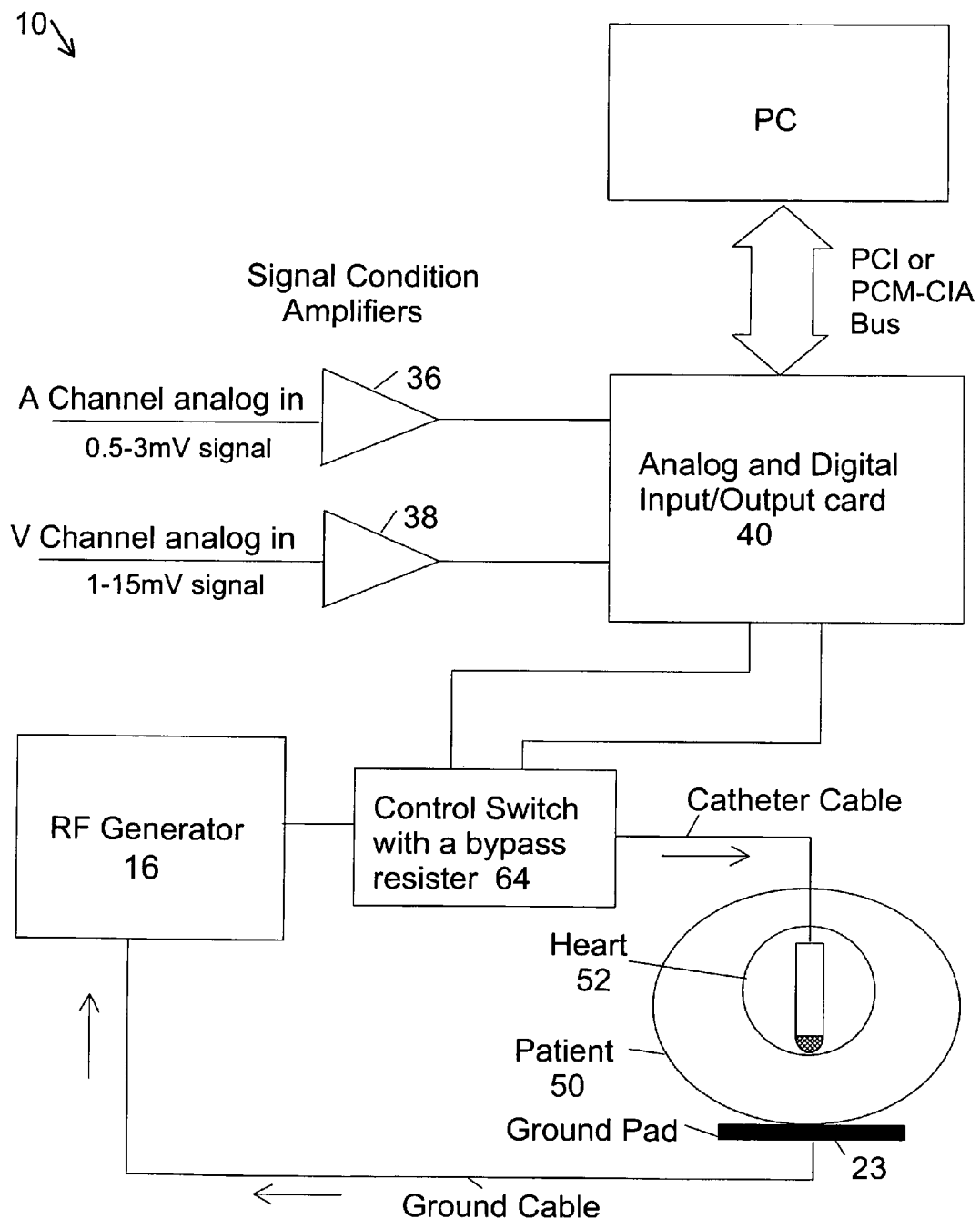

Shown in conjunction with FIGS. 4, 5A, and 5B are simplified block diagrams of the current invention, which is referred to as Ablation Interface Device (AID) 10. As was shown in FIG. 3, atrial signal from high right atrium (HRA) and ventricular signal from right ventricle (RV) are brought in the Ablation Interface Device (AID) 10 by splitting the signal from the junction box 12. Atrial signals which are typically in the 0.5 mV to 3 mV range, and ventricular signals which are typically in the 1-15 mV range, are isolated from the patient 50 using standard techniques known in the art. Signal conditioning such as amplification and filtering is also performed using standard amplification and filtering techniques. From signal conditioning amplifier 36, 38 the signal is connected to a data acquisition system 40 for bringing the two channel information for processing and analyzing the signals. The DAQ system may be a plug-in board for a desktop PC, a plug-in PCM-CIA card for a laptop, or an external DAQ unit connected to the PC or laptop via a fast USB port. All of these data acquisition systems are available from National Instruments Corp. (Austin, Tex.), and other manufacturers.

The conditioned signals, i.e. the high right atrial (HRA) and ventricular (V) recording, are analyzed real time using the processor and software in the laptop PC or desktop PC. The software analyzes the information from the intra-cardiac recording real-time. When the pre-determined criteria are met, i.e. where the safety of ablation is in question, the computer will automatically stop the delivery of ablation energy to the patient, whether its RF ablation, cryoablation, or any other form of ablation energy. Advantageously, computer controlled operations will be much quicker, and in many cases will prevent the patient from getting heart blocked, and pacemaker implanted.

As shown in conjunction with FIG. 4, under appropriate pre-determined conditions, the computer may turn off the power supply of the RF generator or the cryoablator via a relay switch. Shown in conjunction with FIG. 5A, the control switch 62 may be adapted to be placed between the ground cable and the RF generator 16. RF generators typically monitor the impedance of the circuit. If the impedance increases above a specified level, or if the generator detects an open circuit, the RF generator will shut off immediately, and the ablation generator will display an error message. Alternatively, shown in conjunction with FIG. 5B a control switch 64 with a bypass resister may be adapted to be placed between the RF generator and the ablation catheter.

Figure 6:
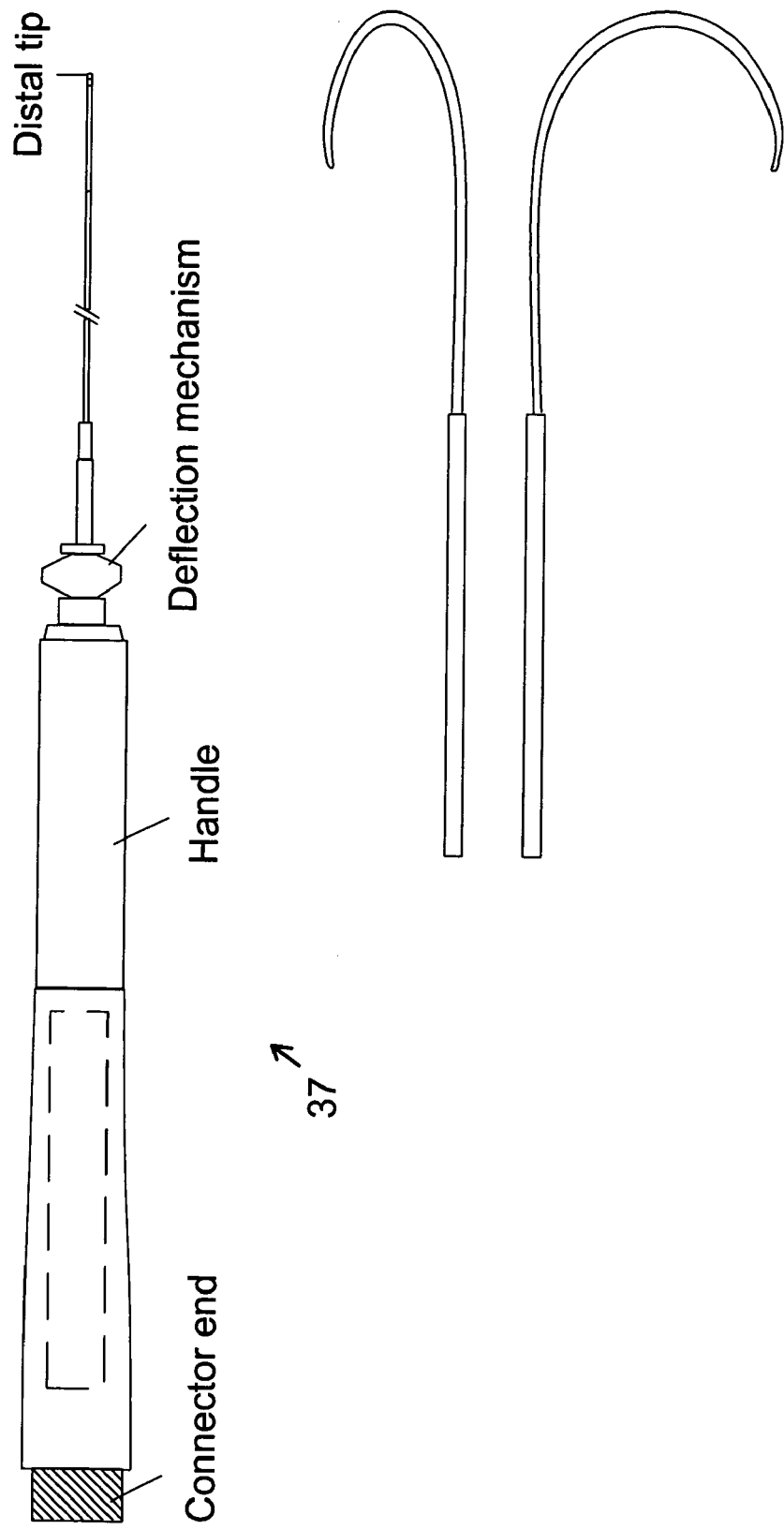
FIG. 6 is a diagrammatic representation of a generic ablation catheter.

Shown in conjunction with FIG. 6, standard deflectable tip ablation catheter 37 from any manufacturer may be used (RF or Cryo). Ablation catheters adapted to be used with RF ablation and cryoablation are well known in the art.

AVNRT Ablation Procedure

Figure 7:
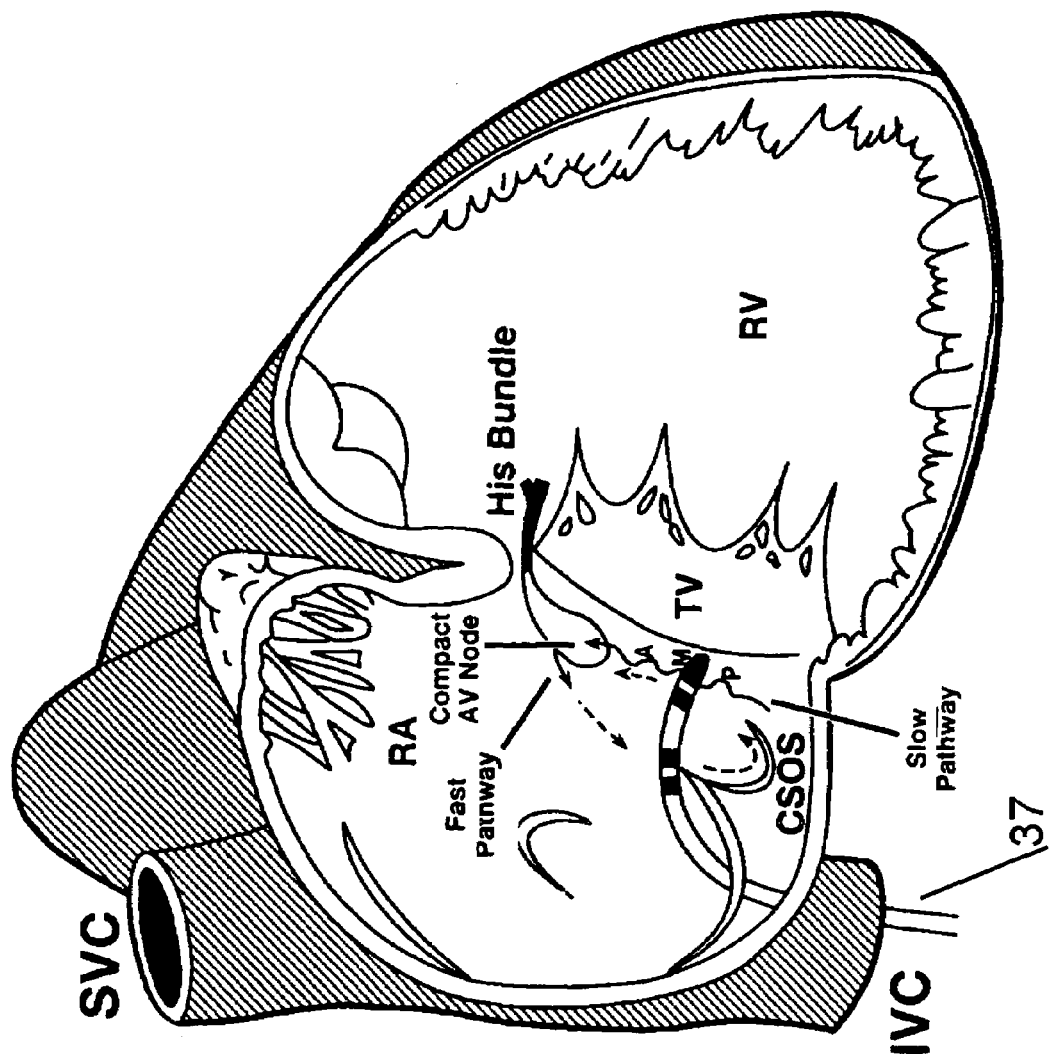
FIG. 7 shows anatomy of the heart that is relevant to AVNRT ablation.
Figure 8:
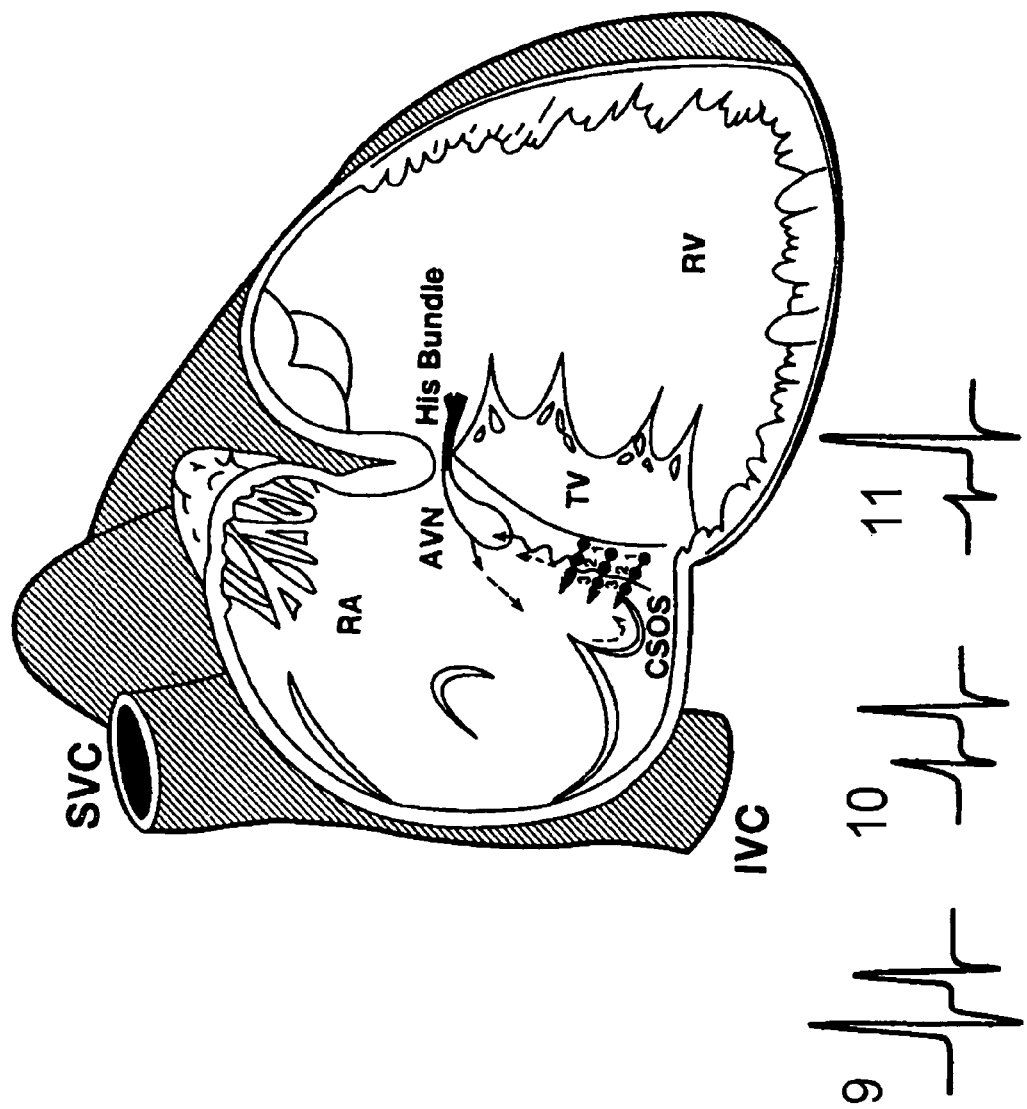
FIG. 8 shows anatomy of the heart relevant to AVNRT, along with corresponding intra-cardiac electrograms.

For AVNRT ablation procedure, the catheter tip is positioned at the appropriate site in the heart based on anatomic landmarks, and electrogram recording from the tip of the ablation catheter, as seen on the EP recording system. FIG. 7 shows placement of the catheter tip based on His bundle and os of the coronary sinus (CS). FIG. 8 shows the anatomy of the relevant area along with some samples of the intracardiac recordings on the bottom.

Figure 9:
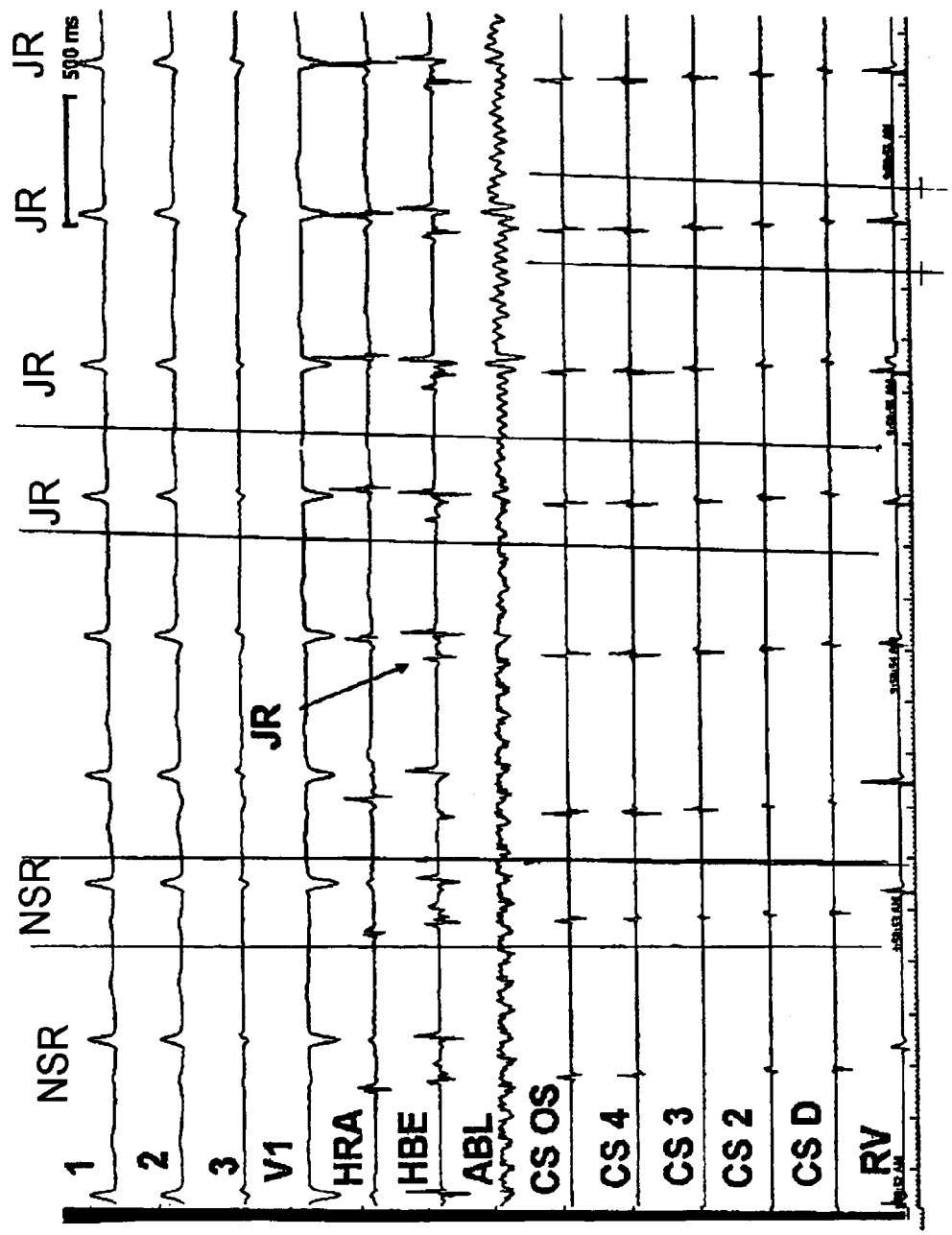
FIG. 9 is a rhythm strip showing normal sinus rhythm (NSR) and junctional rhythm (JR), during AVNRT ablation procedure.
Figure 10:
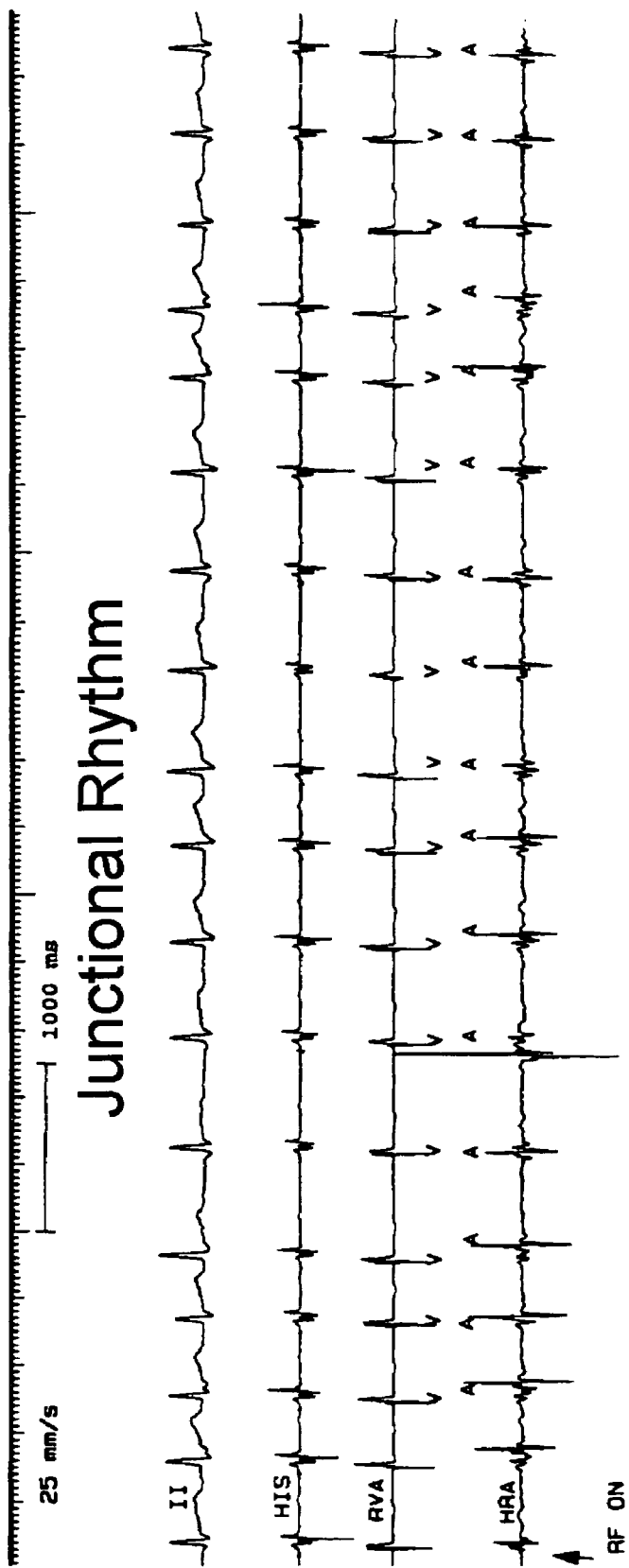
FIG. 10 is a rhythm strip showing junctional rhythm (JR) during AVNRT ablation procedure.

As the ablation energy is applied, the normal sinus rhythm (NSR) is at some point converted to junctional rhythm (JR). This is shown in conjuction with FIG. 9. When RF ablation is used, this is due to local heating of the tissues. If the junctional rhythm is a slow junctional rhythm, and if the A's and V's are always associated, then the ablation is proceeding very nicely. The first two beats in FIG. 9 labeled NSR, are normal sinus beats. Starting with the fourth beat labeled JR, and the rest of the beats are junctional rhythm (JR) beats. FIG. 10, also shows junctional beats where the A's and V's are associated.

It is very important in AVNRT ablations that the RF energy is immediately stopped when;

there is loss of retrograde conduction, rapid junctional rhythm occurs, or an increase in the PR interval occurs.

Sometimes the human reaction is not fast enough, and the patient inadvertently ends up with complete heart block (CHB), and subsequent pacemaker implant. It is even more distressing when the patient is relatively young, as is frequently the case.

In order to avoid this, or at least minimize the chances of inadvertent heart block from occurring, the atrial (A) and ventricular (V) signals are analyzed by the computer of AID 10 (FIGS. 4, 5A, 5B) system.

Signal Analysis by Software

Program code can be written using one of several commercially available software packages. The software can be written utilizing development tools and graphical programming applicants or languages such as LAB WINDOWS/CVI®, LAB VIEW® (National Instruments Corp.), MICROSOFT VISUAL C++®, DOT NET FRAMEWORK®, MATLAB®, MICROSOFT VISUAL BASIC®, among others. Use of these or other comprable languages for this purpose that are available now or developed in the future, is considered within the scope of the invention. Testing of applicant's prototype has been performed using both MICROSOFT VISUAL C++®, and LAB VIEW®.

Shown in conjunction with FIGS. 11A-11F are different scenarios that the software installed and configured in AID 10 recognizes and acts upon. It will be clear that these are meant as representative examples and are not to be taken as a limitation.

Figure 11A:
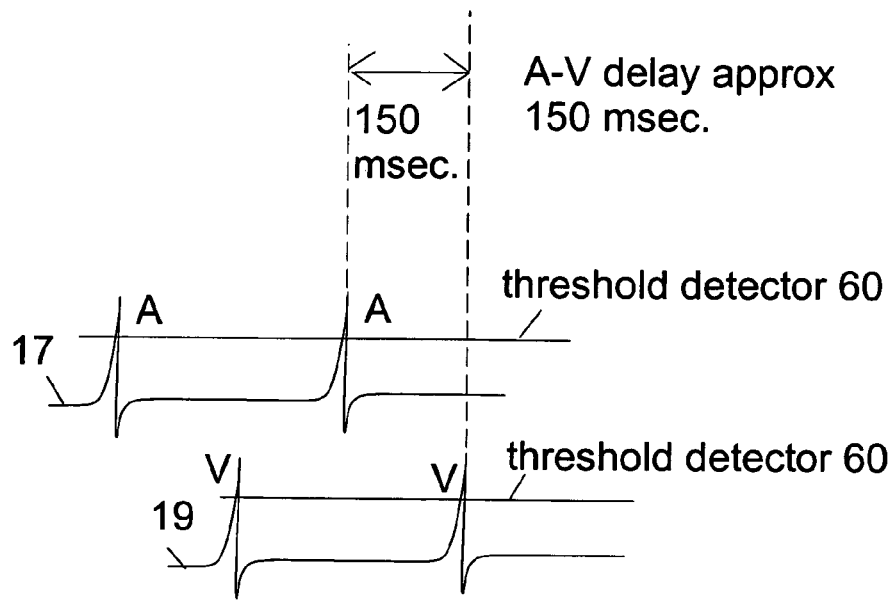
FIG. 11A depicts atrial (A) and ventricular (V) intracardic electrograms showing the timing relationship between A and V during normal sinus rhythm (NSR).
Figure 11B:
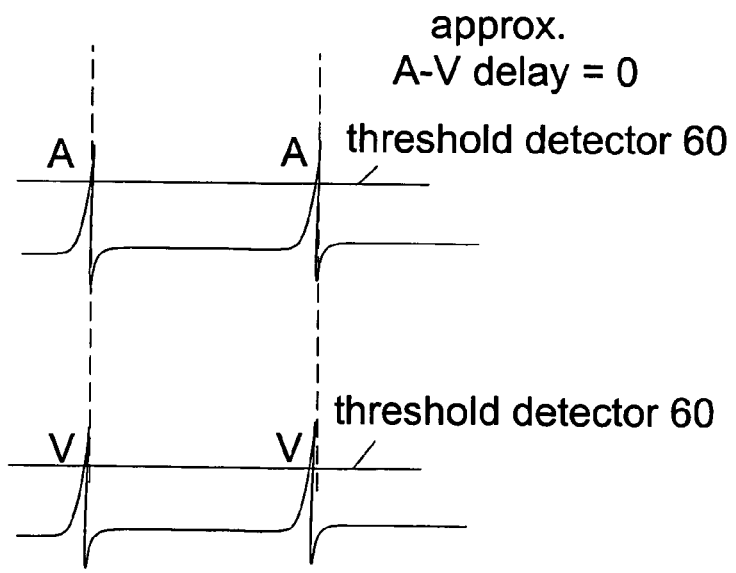
FIG. 11B depicts atrial (A) and ventricular (V) intracardic electrograms showing the timing relationship between A and V during junctional rhythm (JR).

Before the ablation energy is applied, the patient is in normal sinus rhythm (NSR), which is depicted in FIG. 11A. Based on a threshold detector 60, when an atrial (A) signal is detected, it starts a counter and waits for a ventricular (V) signal within a pre-determined interval, say 200 msec. When the patient is in NSR, there will be ventricular beat within the specified interval, and the counter will reset. This sequence will keep getting repeated.

When the ablation energy is applied, at some point the patient's rhythm will go into junctional rhythm (JR). This is shown with reference to FIG. 11B. During the junctional rhythm, the A signal and V signal will be triggered approximately simultaneously. Sometimes the A will be triggered just before the V, or the V will be triggered just before the A. As long as, both A and V are triggered as a pair, and within a pre-determined interval, the counter will keep resetting, and the software will be in "watch" mode only, without taking any action.

Figure 11C:
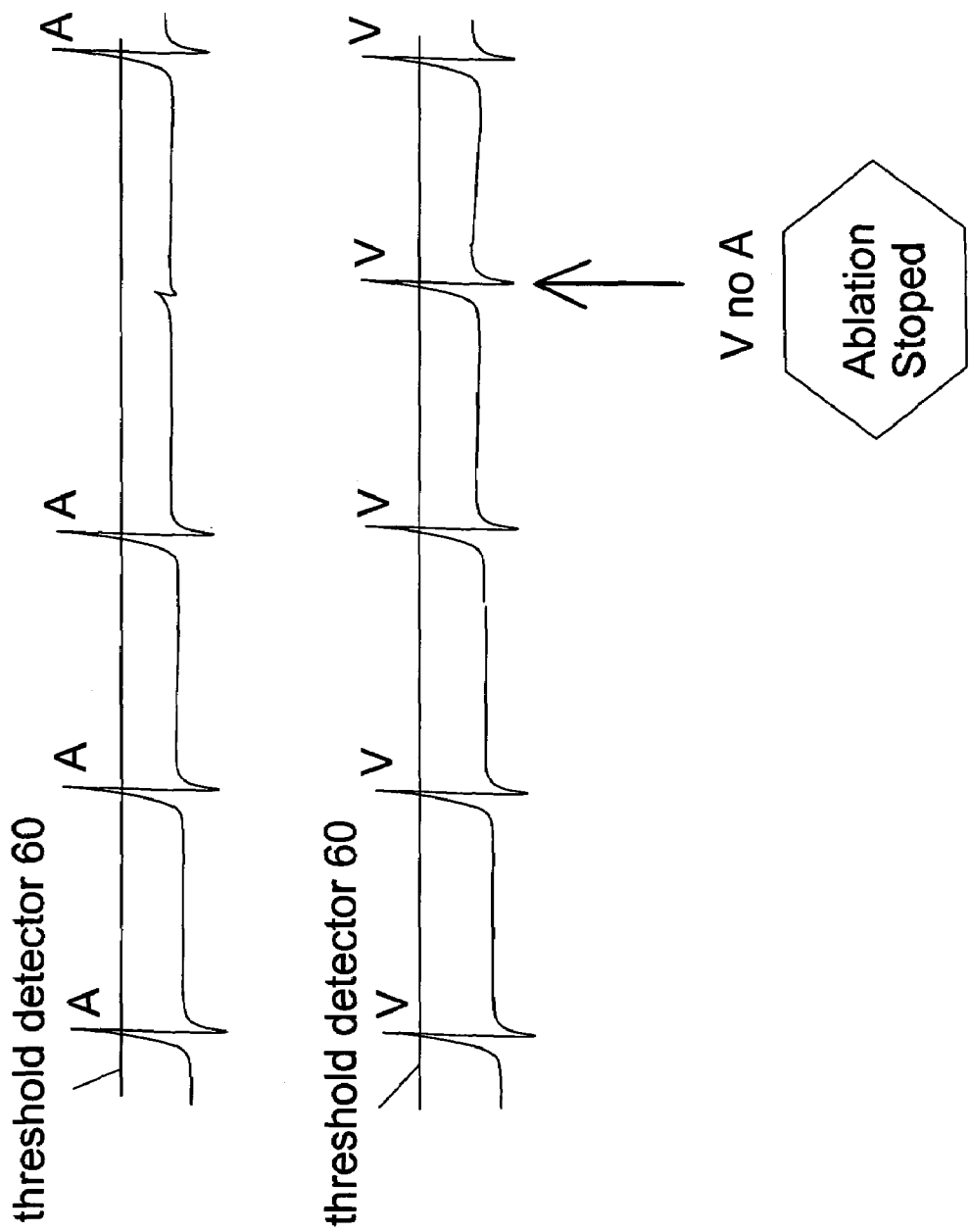

As shown in conjunction with FIG. 11C, if the software detects a V signal, and no A signal is detected within a pre-determined interval, that implies loss of retrograde conduction, which triggers a flag, and the ablation circuit is immediately opened, or the ablation power is cut-off. Advantageously, when seconds are important, the software guided instrumentation can react much quicker than human reaction, especially since more than one person is typically involved in the loop. Shown in conjunction with FIG. 11D is a depiction, where during "slow" junctional rhythm, an A is detected with no V detected within a pre-determined window. Again, like the scenario depicted in FIG. 11C, a flag is triggered and the ablation is immediately halted.

Figure 12:
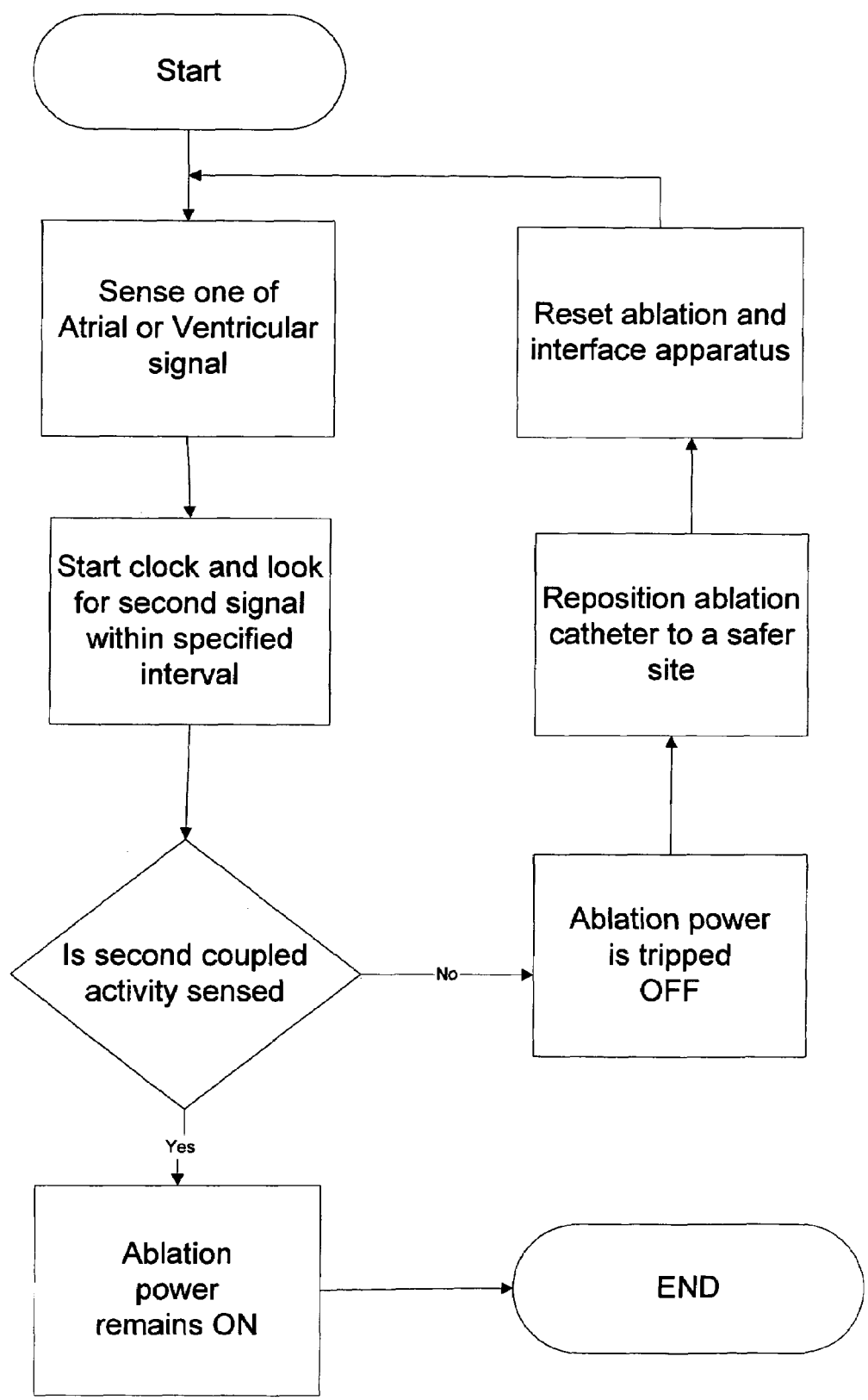
FIG. 12 is flow diagram showing the logic behind the ablation being stopped automatically.

Also summarized in the flow diagram of FIG. 12, when either A or V event is sensed, a counter is initiated for pre-determined interval to look for the corresponding other signal. In other words if A event is detected, then the instrumentation is expecting a V event, if a V event is detected the instrumentation is "looking" for an A signal within a specified interval. If a paired activity is sensed (both A and V), the counter keeps resetting. In the event, a second coupled activity is not sensed, the ablation circuit is tripped off. After such an event, the ablation catheter is repositioned to a safer spot and the ablation procedure is once again continued.

Figure 11E:
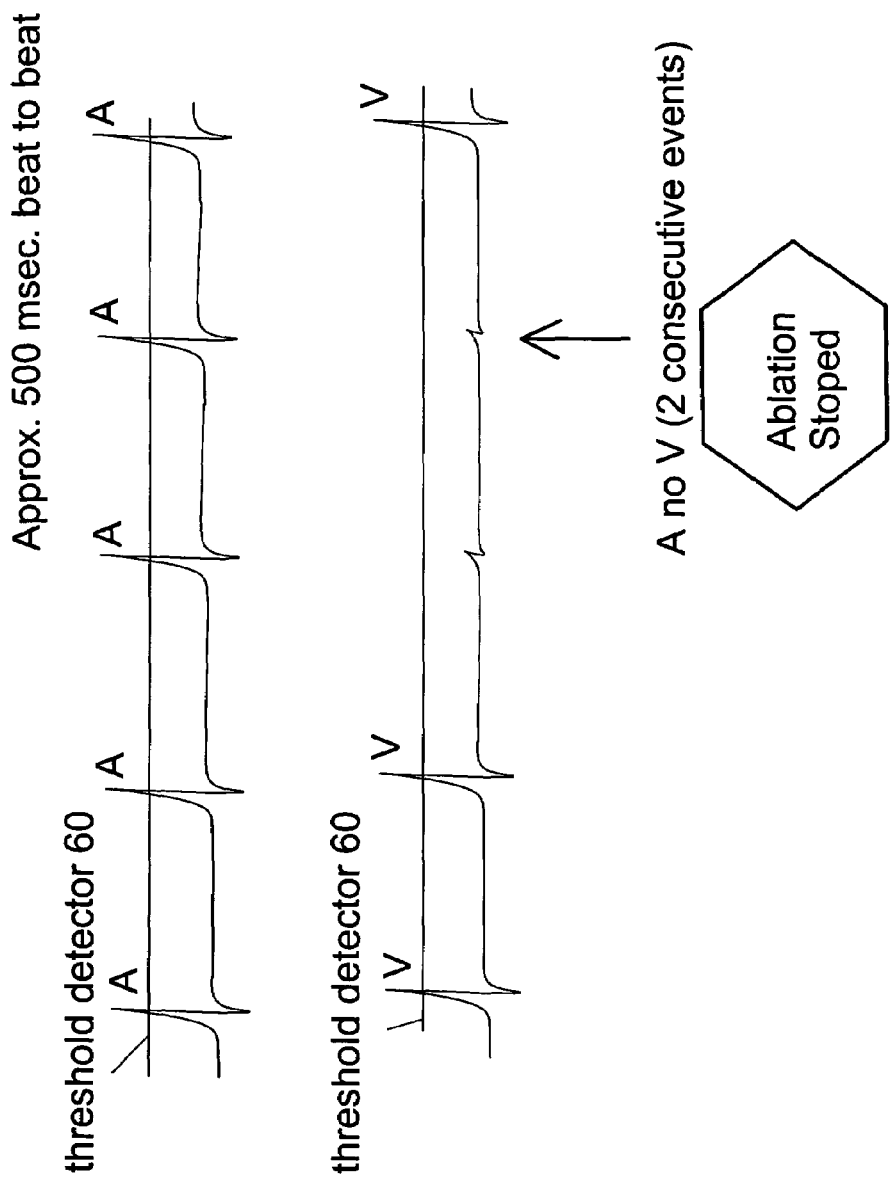
FIG. 11E shows a flag being triggered at the second dropped beat during fast junctional rhythm.

Sometimes the junctional rhythm is somewhat faster, and the physician may program the instrumentation to stop the ablation either at the first dropped V or at the second dropped V as is shown in conjunction with FIG. 11E. Of course, if the junctional rate becomes too fast (based on a pre-determined interval, the instrument will automatically trigger to stop the ablation, so the catheter can be repositioned to a more safer location.

Figure 11F:
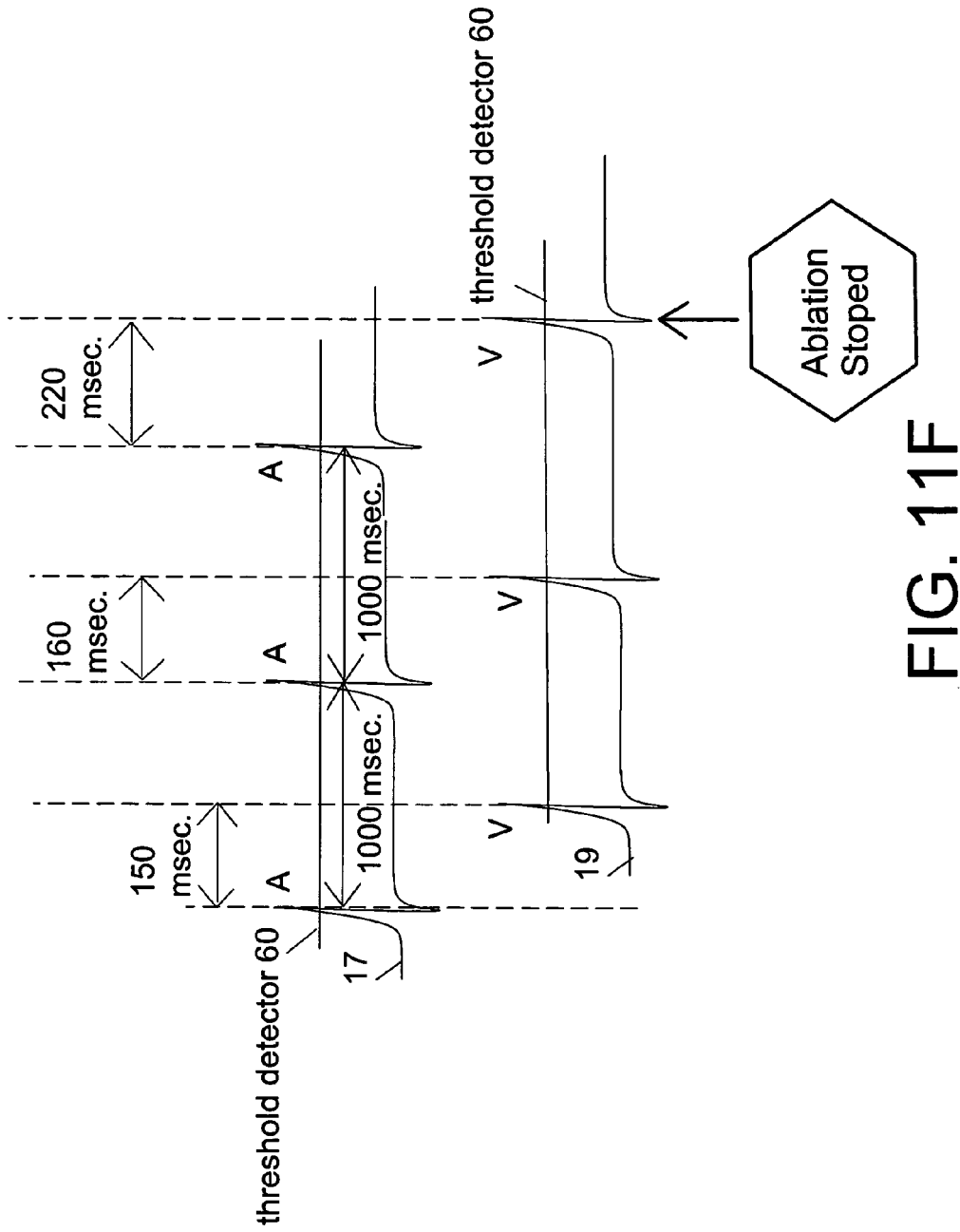
FIG. 11F depicts prolonged A-V interval during ablation, triggering a flag.

FIG. 11F depicts a scenario, where the instrumentation stops the ablation procedure if the P-R interval, i.e. time between A event and V event exceeds a predetermined interval.

In the presently preferred embodiment, the software is configured, such that the pre-determined intervals can be easily adjusted, or custom programmed for each physician. Also, if the instrumentation triggers on a false-positive event, a reset button is clicked, and the procedure proceeds without delay.

Figure 13A:
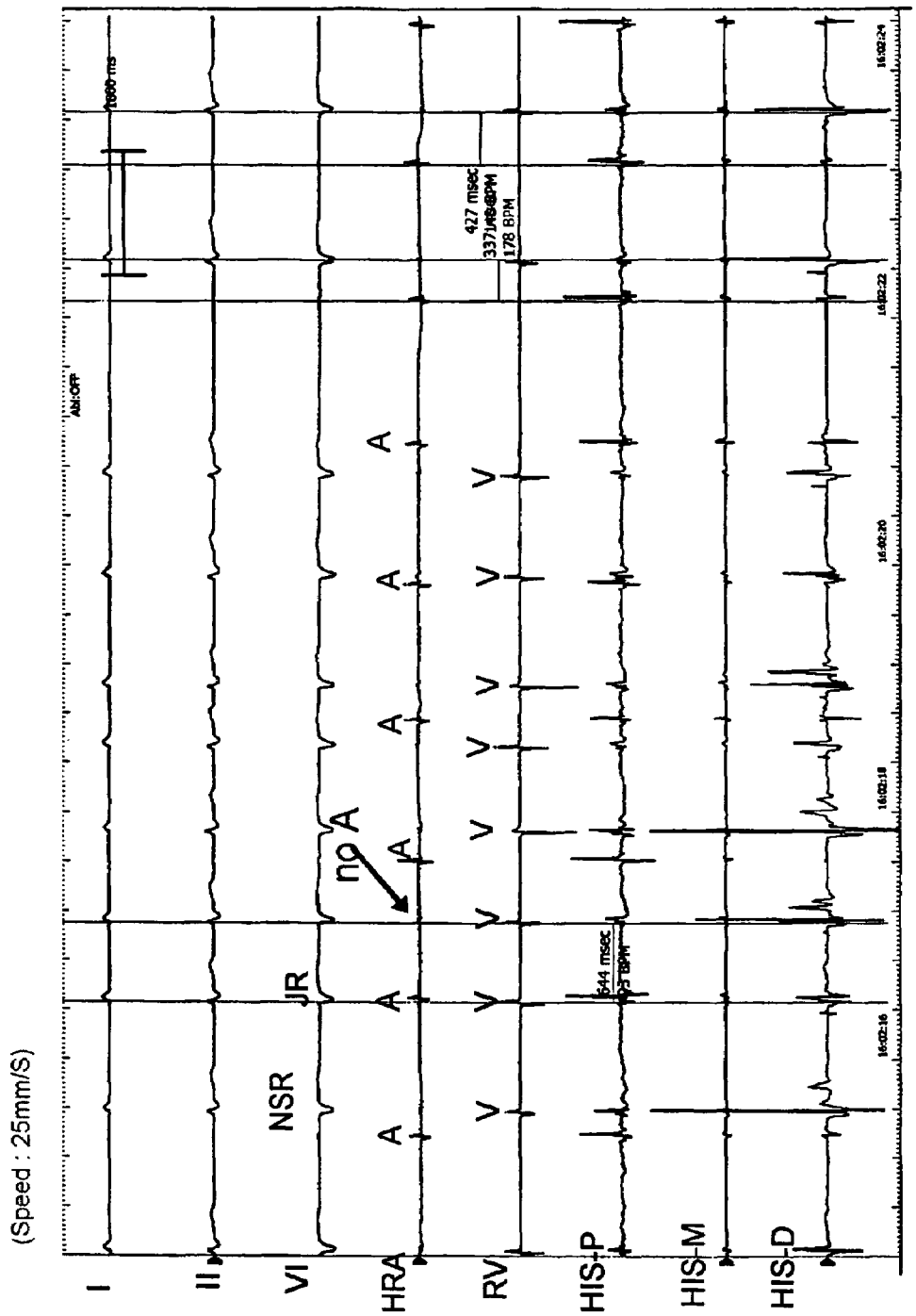
FIGS. 13A-13C are rhythm strips from an actual ablation procedure where the patient went into complete heart block (CHB).
Figure 13B:
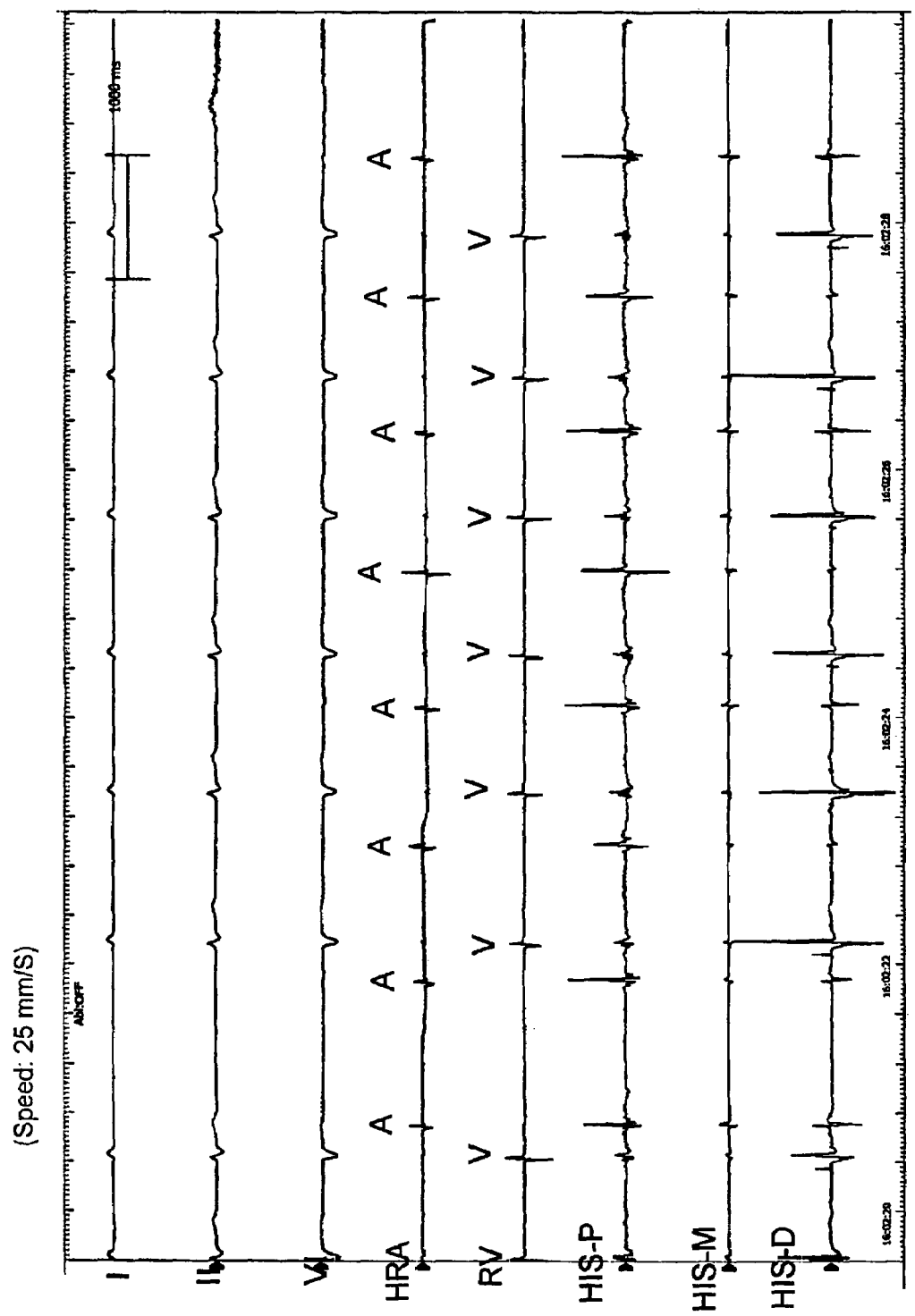
Figure 13C:
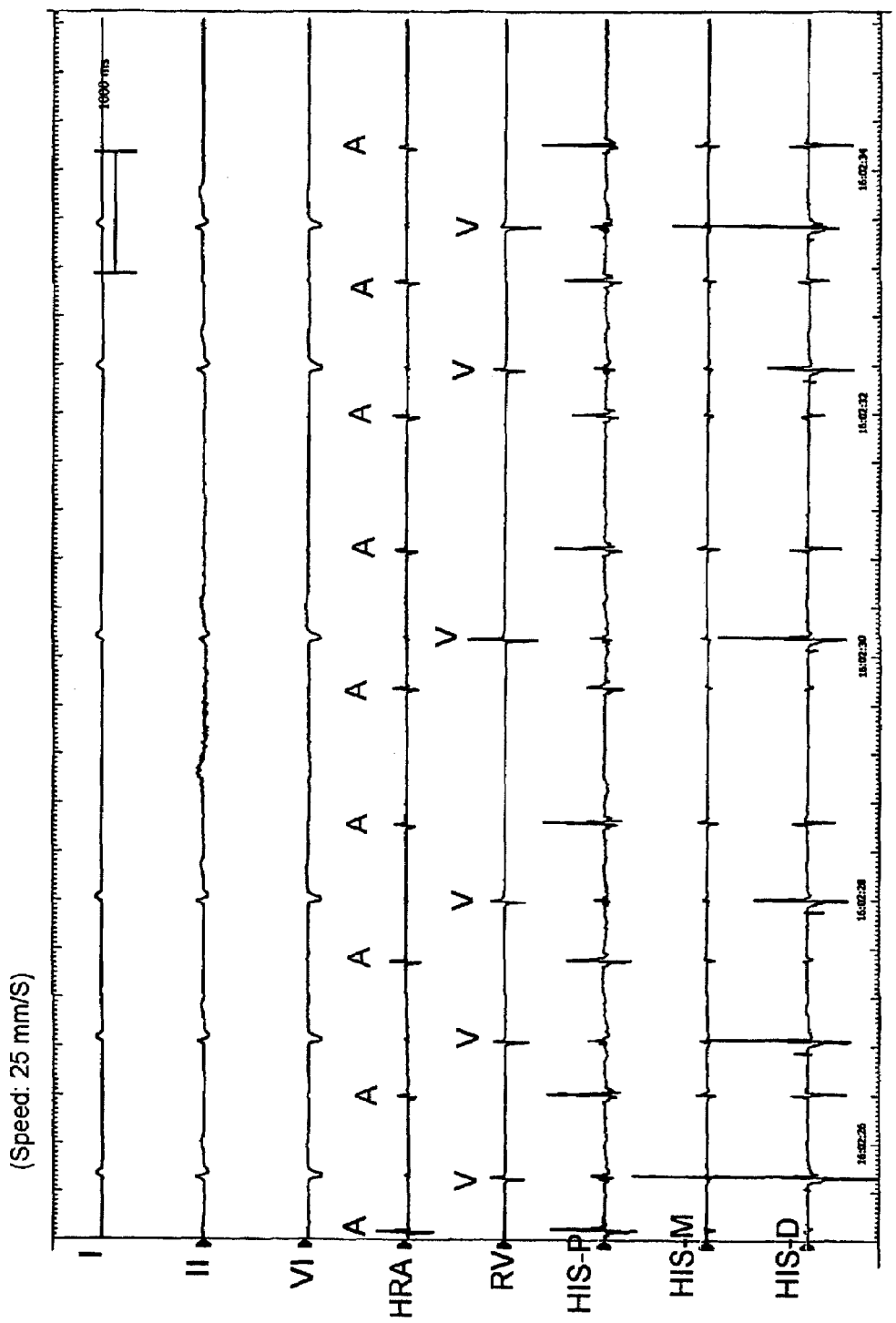

Shown in conjunction with FIGS. 13A, 13B, and 13C is an example of a real AVNRT ablation case, where a complete heart block (CHB) occurred in a patient, which could have been prevented with the method and system of the current invention. As shown in FIG. 13A, the first beat on the left labeled NSR is a sinus beat. The second beat labeled JR is a junctional beat since the A and V occur almost simultaneously. The third beat comprises V and no A. Using the AID 10, of this invention, the ablation energy would have been turned off within milliseconds. But since the human reaction time is much slower, between the physician deciding to turn off the ablation, and communicating this with the technician operating the ablation device, it took nearly 4 seconds. As shown in strips 13B and 13C, which are continuous (the time is stamped on the bottom), that complete heart block (CHB) follows. The A events and V events are dissociated, with no relationship between them. This is particularly evident in the second half of strip 13C.

Figure 14:
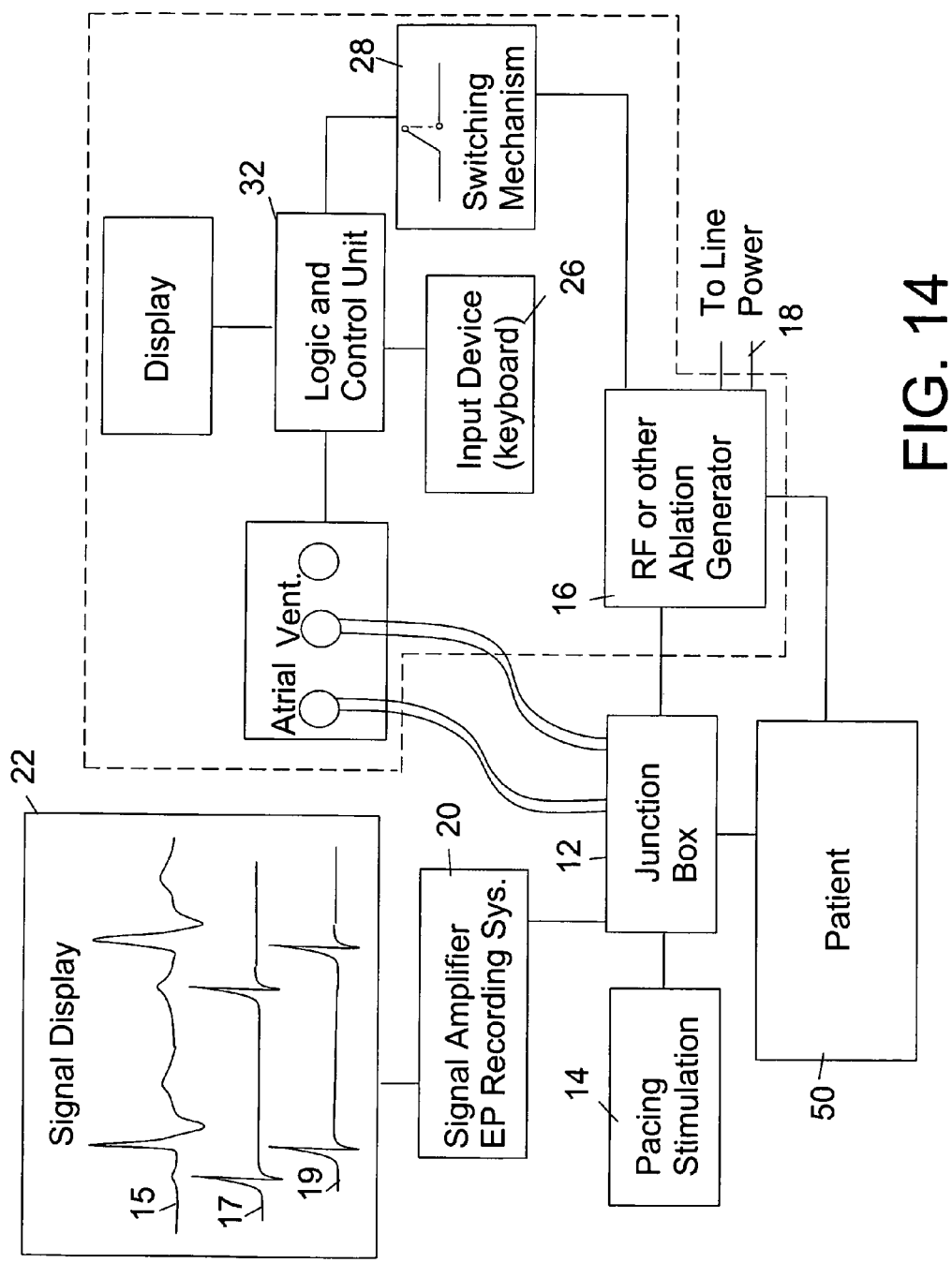
FIG. 14 is a simplified block diagram depicting the functionality of the invention being incorporated into an ablation generator.
Figure 15:
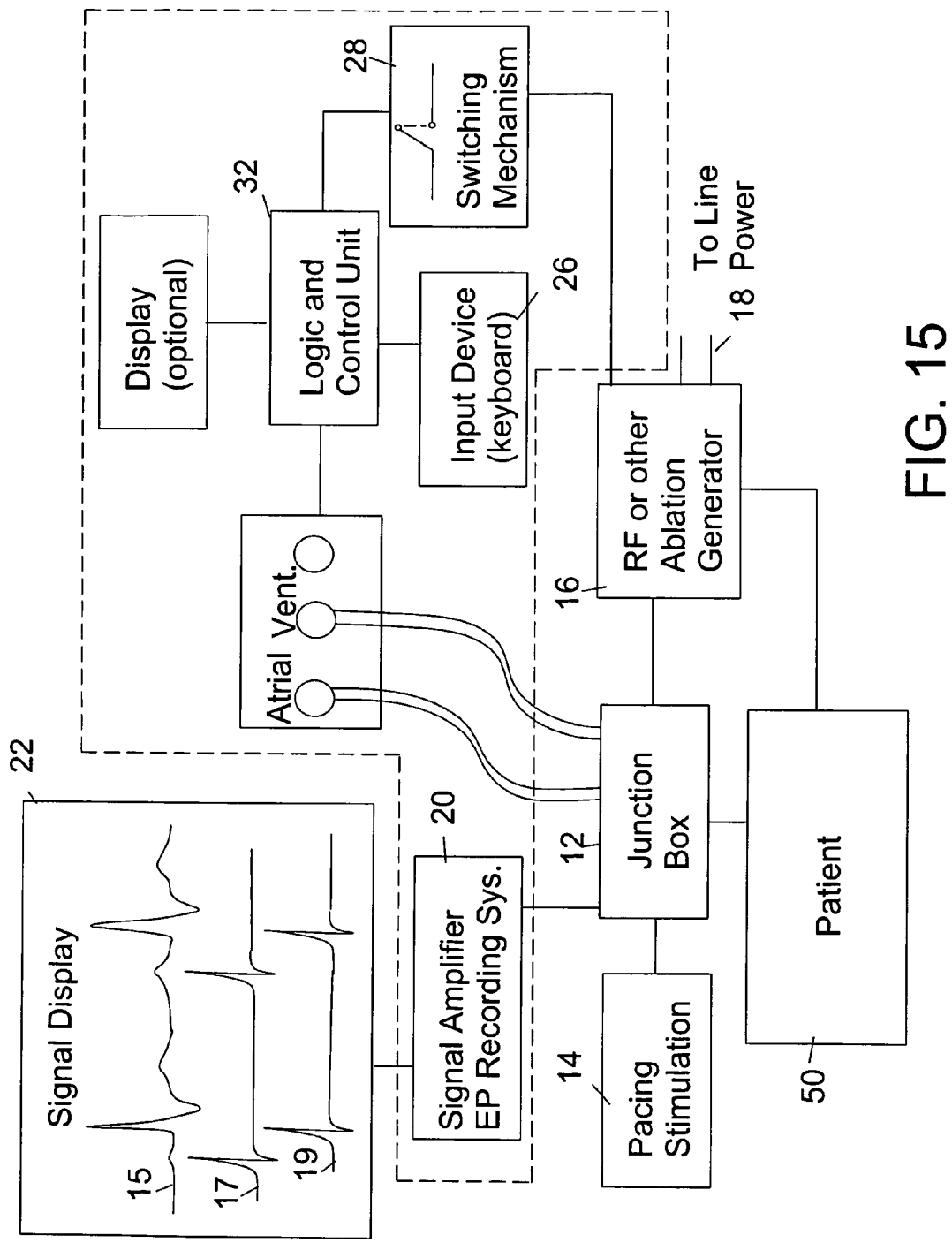
FIG. 15 is a simplified block diagram depicting the functionality of the invention being incorporated into an electrophysiology (EP) monitoring system.

It will be clear to one of ordinary skill in the art, that the AID 10 circuitry and ablation generator circuitry can be combined within the same enclosure for convenience, as is shown in the simplified block diagram of FIG. 14. I.e., a combined "smart" generator would have application for ablation of AVNRT and other cardiac ablation procedures such as ablation for atrial fibrillation. Alternatively, as shown in the simplified block diagram of FIG. 15, the AID system of the current invention may also be incorporated within an EP monitoring system, such as the Pruca system of GE Medical (Miwaukee, Wis.). An AID 10 particularly useful for left sided atrial fibrillation ablation procedure is disclosed in a separate application.

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

We claim:

1. A method of increasing safety of cardiac ablation procedures, comprising the steps of:

aquiring atrial and ventricular intracardiac signals of a patient into a computer;

conditioning said atrial and ventricular intracardiac signals;

performing timing analysis of a patient's said atrial and ventricular intracardiac signals utilizing a software program capable of performing said timing analysis of said atrial and ventricular intracardiac signals in substantially real-time or near real-time and further comprises pairing of each said ventricular signal with each atrial signal;

detecting an event indicative of an imminent heart block in said patient utilizing said software program wherein said event is the first (A-V) dropped beat or the first A-V dissociation; and stopping automatically energy delivery of said ablation procedure based upon said timing analysis performed substantially real-time or near real-time.

2. The method of claim 1, wherein said software program can be written utilizing development tools and graphical programming applications or languages such as LAB WINDOWS®/CVI, LABVIEW® (NATIONAL INSTRUMENTS CORP.), MICROSOFT VISUAL C++®, DOT NET FRAMEWORK®, MICROSOFT VISUAL BASIC®, or functionally equivalent software.

3. The method of claim 1, wherein said stopping energy delivery of said ablation procedure via at least one of:
   i) a ground patch connection, or
   ii) an ablation catheter connection.

4. The method of claim 1, wherein said ablation procedure is for AV nodal reentry tachycardia (AVNRT) ablation or for an antero-septal accessory pathway ablation.

5. The method of claim 1, wherein said cardiac ablation procedure is at least one of: a RF ablation, a cyroablation, or a high intensity focused ultrasound (HIFU) ablation.

6. The method of claim 1, wherein said event further comprises at least one of: a loss of retrograde condition, an increase in the PR interval, or rapid junction rhythm.

7. The method of claim 1, wherein said first (A-V) dropped beat is an atrial (A) signal which is not associated with a ventricular (V) signal.

8. The method of claim 1, wherein said first (A-V) dropped beat is a ventricular (V) signal which is not associated with an atrial (A) signal.

9. A method of increasing safety of a cardiac ablation procedure by preventing or decreasing heart block of a patient, comprising the steps of:

monitoring in real time or near real time, atrial and ventricular intracardiac signals of a patient by acquiring said atrial and ventricular intracardiac signals of a patient into a computer, wherein said acquiring comprises acquisition, conditioning and analog to digital conversion means for said signals, providing software configured for performing and utilizing timing analysis of said atrial and ventricular intracardiac signals in said computer, performing said timing analysis of said atrial and ventricular intracardiac signals, and detecting an event indicative of an imminent heart block in said patient based on said timing analysis of said atrial and ventricular intracardiac signals wherein said event is the first (A-V) dropped beat or the first A-V dissociation; and stopping automatically the energy delivery of said ablation procedure.

10. The method of claim 9, wherein said method may be incorporated into or combined with or embedded with an ablation generator.

11. The method of claim 9, wherein said method may be incorporated into or combined with or embedded with an electrophysiology recording system.

12. The method of claim 9, wherein said software program can be written utilizing development tools and graphical programming applications or languages such as LAB WINDOWS®/CVI, LABVIEW® (NATIONAL INSTRUMENTS CORP.), MICROSOFT VISUAL C++®, DOT NET FRAMEWORK®, MICROSOFT VISUAL BASIC®, or functionally equivalent software.

13. The method of claim 9, wherein said stopping energy delivery of said ablation procedure via at least one of:
   i) a ground patch connection, or
   ii) an ablation catheter connection.

14. The method of claim 9, wherein said ablation procedure is for AV nodal reentry tachycardia (AVNRT) ablation or for an antero-septal accessory pathway ablation.

15. The method of claim 9, wherein said cardiac ablation procedure is at least one of: a RF ablation, a cyroablation, or a high intensity focused ultrasound (HIFU) ablation.

16. The method of claim 9, wherein said first (A-V) dropped beat is an atrial (A) signal which is not associated with a ventricular (V) signal.

17. The method of claim 9, wherein said first (A-V) dropped beat is a ventricular (V) signal which is not associated with an atrial (A) signal.

* * * * *